(12) United States Patent
Zimmerman et al.

(10) Patent No.: US 12,193,417 B2
(45) Date of Patent: Jan. 14, 2025

(54) HERD FEEDING SYSTEM WITH LOW-COST, EFFICIENT, AND PORTABLE FEED BINS FOR FEEDING INDIVIDUAL ANIMALS

(71) Applicant: C-LOCK INC., Rapid City, SD (US)

(72) Inventors: Patrick R. Zimmerman, Rapid City, SD (US); Robert Scott Zimmerman, Rapid City, SD (US); James R. Krause, Spearfish, SD (US); Mike Billars, Rapid City, SD (US)

(73) Assignee: C-Lock Inc., Rapid City, SD (US)

( * ) Notice: Subject to any disclaimer, the term of this patent is extended or adjusted under 35 U.S.C. 154(b) by 1097 days.

(21) Appl. No.: 17/072,828

(22) Filed: Oct. 16, 2020

(65) Prior Publication Data

US 2021/0127630 A1    May 6, 2021

Related U.S. Application Data

(60) Provisional application No. 62/929,217, filed on Nov. 1, 2019.

(51) Int. Cl.
*A01K 5/02*     (2006.01)
*A01K 11/00*   (2006.01)
(Continued)

(52) U.S. Cl.
CPC .......... *A01K 5/0283* (2013.01); *A01K 5/0258* (2013.01); *A01K 5/0291* (2013.01);
(Continued)

(58) Field of Classification Search
CPC ...... A01K 5/02; A01K 5/0258; A01K 5/0283; A01K 5/0291; A01K 11/004; A01K 29/005; A01K 5/01; A01K 5/0275
See application file for complete search history.

(56) References Cited

U.S. PATENT DOCUMENTS

| 4,350,119 A | * | 9/1982 | Ostler | .................. A01K 11/006 |
| | | | | 119/51.02 |
| 4,461,241 A | * | 7/1984 | Ostler | .................. A01K 11/006 |
| | | | | 119/51.02 |

(Continued)

FOREIGN PATENT DOCUMENTS

| EP | 0272716 A | 6/1988 |
| GB | 2190574 A | 11/1987 |

(Continued)

OTHER PUBLICATIONS

International Search Report PCT/US2020/056088, Jan. 21, 2021.

*Primary Examiner* — Yvonne R Abbott-Lewis
(74) *Attorney, Agent, or Firm* — Snell & Wilmer LLP

(57) ABSTRACT

A feeding system for feeding individual animals of a herd feed, supplements, and combinations thereof. The feeding system includes one-to-many feed bin assemblies or feeding stations such that the system is able to dispense a specified mass of feed to specific animals at user-defined intervals. In this way, each animal of a herd is provided with optimal, individualized amounts of feed or feed material. Multiple feed bin assemblies in a single pasture, for example, can automatically form a network of feeders so that regardless of the specific feed bin assembly or feeding station within the feeding system that an animal visits, the specified amount and type of feed or feed material is delivered. Each feed bin assembly or feeding station can also be equipped to download, archive/store, and/or synthesize data into an individual animal record and/or to transmit data from additional onboard animal sensors such as activity and rumination sensors.

23 Claims, 6 Drawing Sheets

(51) Int. Cl.
  *A01K 29/00*    (2006.01)
  *A61B 5/01*     (2006.01)
  *A61B 5/08*     (2006.01)
  *A61B 5/11*     (2006.01)
  *G08C 17/00*    (2006.01)
(52) U.S. Cl.
  CPC .......... *A01K 11/004* (2013.01); *A01K 29/005* (2013.01); *A61B 5/01* (2013.01); *A61B 5/082* (2013.01); *A61B 5/1118* (2013.01); *G08C 17/00* (2013.01); *A61B 2503/40* (2013.01)

(56) References Cited

U.S. PATENT DOCUMENTS

| | | | |
|---|---|---|---|
| 4,735,171 | A | 4/1988 | Essex |
| 6,427,627 | B1* | 8/2002 | Huisma .................. A01K 5/02 |
| | | | 119/51.02 |
| 6,868,804 | B1* | 3/2005 | Huisma ................. A01K 29/00 |
| | | | 119/842 |
| 7,415,418 | B2 | 8/2008 | Zimmerman |
| 7,966,971 | B2 | 6/2011 | Zimmerman |
| 8,307,785 | B2 | 11/2012 | Zimmerman et al. |
| 8,453,601 | B2 | 6/2013 | Zimmerman |
| 10,085,419 | B2 | 10/2018 | Zimmerman et al. |
| 2003/0084853 | A1* | 5/2003 | Voogd ................. A01K 5/0275 |
| | | | 119/51.02 |
| 2005/0217591 | A1* | 10/2005 | Turner ................ A01K 5/0114 |
| | | | 119/51.02 |
| 2007/0137584 | A1* | 6/2007 | Travis .................... A01K 5/02 |
| | | | 119/51.02 |
| 2007/0181068 | A1* | 8/2007 | McKeown ............... A01K 5/02 |
| | | | 119/51.02 |
| 2009/0126640 | A1* | 5/2009 | Ulman ................ A01K 5/0275 |
| | | | 340/573.3 |
| 2011/0297090 | A1* | 12/2011 | Chamberlain ....... A01K 5/0291 |
| | | | 119/51.02 |
| 2012/0089340 | A1* | 4/2012 | Huisma .............. G01G 19/4146 |
| | | | 702/19 |
| 2015/0181838 | A1* | 7/2015 | Epema ................. G01L 5/0052 |
| | | | 119/58 |
| 2017/0150698 | A1* | 6/2017 | Zaidi .................... A01K 5/0225 |
| 2017/0196203 | A1* | 7/2017 | Huisma ................. G08C 17/02 |
| 2017/0223926 | A1* | 8/2017 | Ausman ............... A01K 11/006 |
| 2017/0290290 | A1* | 10/2017 | Trottier ................ A01K 5/0291 |
| 2022/0232800 | A1* | 7/2022 | Harsh .................. A01K 11/004 |
| 2023/0292705 | A1* | 9/2023 | Snyder .................. G16H 20/60 |
| | | | 119/51.02 |

FOREIGN PATENT DOCUMENTS

| | | |
|---|---|---|
| WO | 8601977 A | 4/1986 |
| WO | 9605723 A | 2/1996 |
| WO | 9622018 A1 | 7/1996 |
| WO | 0038506 A1 | 7/2000 |
| WO | 03032720 A2 | 4/2003 |
| WO | 2012023124 A2 | 2/2012 |
| WO | 2017122097 A1 | 7/2017 |

* cited by examiner

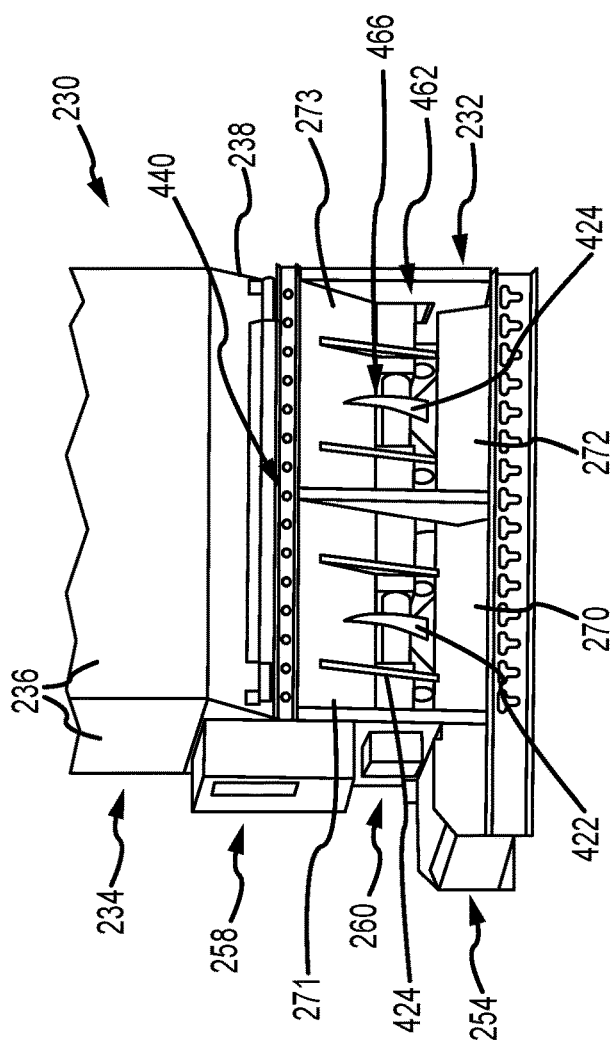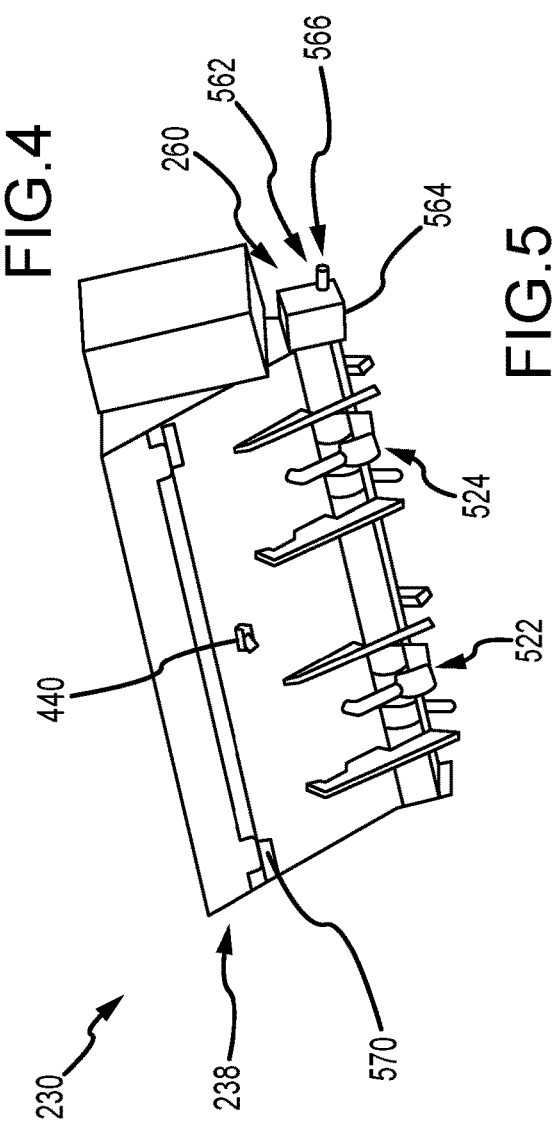

HERD FEEDING SYSTEM WITH LOW-COST, EFFICIENT, AND PORTABLE FEED BINS FOR FEEDING INDIVIDUAL ANIMALS

CROSS-REFERENCE TO RELATED APPLICATION

This application claims the benefit of U.S. Provisional Application No. 62/929,217, filed Nov. 1, 2019 and entitled LOW-COST, EFFICIENT, PORTABLE FEED BIN TO INDIVIDUALLY FEED ANIMALS IN A HERD, which is incorporated herein by reference.

BACKGROUND

1. Field of the Description

The present description relates, in general, to equipment and techniques for feeding herd animals such as beef cattle, dairy cows, sheep, and so on. More particularly, the present description relates to a feed bin that is specially configured to be portable and lower cost to manufacture while being efficient at feeding individual animals of a herd.

2. Relevant Background

In animal agriculture, there commonly is a need to provide specific compound feeds and supplements in the diet (which may be considered "feeding") of each animal in a herd rather than providing the same feeds and supplements to all the herd. Ideally, supplement amounts, composition, and delivery frequency should be provided to each animal based on factors that include its age, sex, weight, life-stage, health, genetics, history, and the production goals for each sub-group and even individual animal within a herd. For example, for beef cattle in a cow-calf operation, the cows that are nursing calves require different nutrients and supplements than maturing heifers intended for breeding. Likewise, maturing steers, bull calves, cattle intended for slaughter, and struggling calves will each have unique nutritional and medicinal requirements. Similarly, in a dairy, lactating cows, fresh-cows just entering their lactation cycle, dry-cows in preparation for breeding, animals that will be grazed in pastures, and those fed a total mixed-ration within a barn will optimally require individual supplementation and treatment as part of feeding a herd.

With this in mind, there is a demand among those in the animal production industry to control the total daily, weekly, and/or monthly intake for each individual animal in their herd. For some animals and to achieve specific production goals, it would likely be advantageous to control the duration of a meal (feeding bout), the amount consumed, the time interval between feeding bouts, and the number of feeding bouts over a specific time interval of minutes, hours, or days. These factors apply to cattle, sheep, horses, pigs, fowl, and other animals of a herd (any group of numerous animals being raised).

Often, though, it is impractical to divide, for optimal feed management, animals into further subgroups, which may include one, two, or more individuals, within the more general herd of like animals. As a result, some animals in a herd or subgroup will overeat while others will not get enough of a particular supplement. Often, all the animals in a group will receive the same treatment when it would be optimal to monitor the animals, and only treat those that exhibit specific symptoms or have certain characteristics (such as lactating, near breeding condition, and so on).

Additionally, in current production facilities, there is usually no ability to monitor and track the feeding behavior of each animal. As a result, there can be significant differences in supplement intake within the animal group. Research has shown that some animals over-consume feed and supplements, and some do not receive enough for optimal production. In beef production pastures, for example, supplementary feed is often dropped directly onto the ground. The result is that significant fractions (e.g., approximately 24 percent) of the feed is simply trampled into the ground and thus wasted. In addition, dominant animals tend to consume much more than their optimal daily requirement. As a result, one "rule of thumb" used in the industry is that to ensure that each animal receives its intended minimum ration approximately twice as much feed as is optimally required must be delivered in total. When bulk supplementation is required, significant amounts of labor and travel are required to deliver the supplement on a daily basis. For animals in remote pastures, travel can be difficult during inclement weather when animals may most need the additional supplementation. Labor can also be difficult to reliably obtain for many animal operations. These inefficiencies result in significant costs to the producer.

Producers purchase rations and supplements of varied composition to achieve a balanced ration at the lowest cost and greatest availability. However, the state of the art for animal feeders is to dispense feed by volume. Optimal animal intake requires the feed to be dispensed based on its mass. The optimal mass delivered is a function of its nutrient density as well as its volumetric density, and these factors can vary, sometimes by two-fold, by feed ingredient, its source, how it is processed, and the time of year. Therefore, significant intake inefficiencies will result if feed is dispensed by volume instead of weight.

Hence, there remains a need for more efficient and effective techniques for feeding or providing feed and/or supplements to a herd of animals. Preferably, the new techniques may be implemented with relatively low cost but durable feed bins that are configured to be portable for locating in various locations on a producer's property and that are configured to operate to dispense feed and/or supplements on an individual animal basis.

SUMMARY

The present invention addresses the above problems by providing a feeding system for feeding animals of a herd feed, supplements, and combinations thereof. The feeding system is relatively inexpensive to implement with respect to the value of the benefits it provides to a producer, and the system may be labeled the SuperSmartfeed (SSF) system. The feeding system is designed to provide a precise amount of feed and supplements (e.g., minerals, medications, and the like) to individual animals in pasture, feedlot, or dairy environments. The examples provided herein relate to its use with cattle for simplicity sake, but it will be understood that the system (with some modifications in some cases) may be used to feed other animals as well such as, but not limited to, dairy cows, sheep, and fowl.

The feeding system includes one-to-many feed bin assemblies or feeding stations such that the system is able to dispense a specified (by an operator, in some cases, or automatically by the system intelligence) mass of feed to specific animals at user-defined intervals. In this way, each animal of a herd is provided with optimal, individualized amounts of feed or feed material, which may be used herein to describe a combination of one or more of feed, supplements, minerals, and medication. Multiple feed bin assemblies (or units) or feeding stations in a single pasture, for example, can automatically form a network of feeders in the feeding system so that regardless of the specific feed bin assembly or feeding station within the feeding system that an animal visits, the specified amount and type of feed or feed material is delivered. Sensors can be provided on or in each feed bin assembly or feeding station to monitor important animal metabolic variables such as carbon dioxide, methane, oxygen, and/or other gases in the animal's breath, internal body temperature of the feeding animal, and respiration sounds. Each feed bin assembly or feeding station can also be equipped to download, archive/store, and/or synthesize data into an individual animal record and/or to transmit data from additional onboard animal sensors such as activity and rumination sensors.

More particularly, an apparatus is provided that is configured for dispensing feed material to individual animals of a herd. The apparatus (or feed bin assembly or SSF feeding station) includes a feed hopper (or feed storage unit) with a first opening for receiving the feed material into an inner space of a body and with second opening for discharging the feed material from bottom of the body. The apparatus also includes a lower support structure supporting the feed hopper and a feed tray in the lower support structure. The apparatus further includes a feed dispensing mechanism operable to selectively dispense the feed material from the feed hopper into the feed tray via the second opening in bottom of the body of the feed hopper. Additionally, the apparatus includes a sensor assembly sensing data for an animal in the herd accessing the feed tray. A controller (e.g., a processor running software to provide functions of a bin control module) processing the data sensed by the sensor assembly to determine an identity of the animal and, in response, to first retrieve based on the identity a predefined mass of the feed material assigned to the animal and to second operate the feed dispensing mechanism to dispense into the feed tray a volume of the feed material determined to provide the predefined mass.

In some embodiments, the sensor assembly includes a weight sensing device determining a weight of the feed hopper. Changes in the weight of the feed hopper are used by the controller to control the feed dispensing mechanism to dispense the volume of the feed material and/or the weight is communicated to a remote device to facilitate refilling the feed hopper with the feed material. In some cases, the sensor assembly includes a weight sensing device for determining a weight of the feed tray, and the controller uses the weight of the feed tray prior to the animal accessing of the feed tray to determine a remaining amount of the feed material and to reduce the volume of the feed material dispensed based on the remaining amount. In these or other implementations, the sensor assembly may include a GPS-based locating device determining a location of the apparatus and wherein the controller wirelessly communicates the location to a remote device to facilitate refilling the feed hopper with the feed material.

The feed dispensing mechanism may include a housing positioned in the lower support structure above the feed tray, and the housing includes one or more openings for receiving the feed from the second opening in the feed hopper. The feed dispensing mechanism further may include an auger positioned within the housing that is selectively rotated by a motor operated by the controller to dispense the volume of the feed material. In such cases, the housing may include a tunnel or pipe through which the auger extends, and the housing can also include a discharge opening providing a passageway from the tunnel to the feed tray. Then, when the auger is rotated by the motor, the auger drives the feed material into the tunnel. The feed dispensing mechanism may further include a hatch and an actuator actuatable by the controller to move from a first position between the discharge opening and the food tray to a second position away from the discharge opening, whereby the food material in the tunnel when the auger is being rotated is dispensed into the food tray.

In some embodiments of the apparatus, it further includes a second feed tray opposite the food tray in the lower support structure, and the feed dispensing mechanism is operable to selectively dispense the feed material from the feed hopper into the second feed tray via the second opening in the feed hopper. The sensor assembly senses data for a second animal in the herd accessing the second feed tray. The controller processes the data sensed by the sensor assembly to determine an identity of the second animal and, in response, to first retrieve based on the identity of the second animal, a predefined mass of the feed material assigned to the second animal, and to second operate the feed dispensing mechanism to dispense into the feed tray a volume of the feed material determined to provide the predefined mass assigned to the second animal. The feed dispensing mechanism further includes a second auger rotated selectively by control signals from the controller to dispense the volume of the feed material via a second discharge opening in the housing. The auger and the second auger are typically arranged to extend horizontally (e.g., relative to planes containing the second and any additional openings) and to be parallel in the housing, and the auger and the second auger are rotated in opposite directions to dispense the feed material from the housing and to keep feed evenly distributed across all discharge openings.

The volume of the feed material can be determined by the controller based on a rotation rate of the auger, a predefined volume per unit rotation for the auger, and a rotation time for the auger during the dispensing of the volume of the feed material by the feed dispensing mechanism. The volume of the feed material may further be determined based on a density of the feed material determined by the controller, prior to operation of the feed dispensing mechanism, based on a weight sensed by the sensor assembly of the feed hopper containing the feed material.

BRIEF DESCRIPTION OF THE DRAWINGS

FIG. 4 is an enlarged view of the lower portion of the feed bin assembly of FIG. 2 during operations with feed tray doors or covers over the front two feed trays being lifted to expose feed hatches;

FIG. 5 is rear partial and enlarged perspective view of the feed bin assembly of FIGS. 2-4 showing features of the feed dispensing mechanism;

DETAILED DESCRIPTION

Embodiments described herein are directed toward a new feeding system for providing feed material (which may include feed, supplements, and combinations thereof) on an animal-by-animal basis to a herd of animals such as cattle. The feeding system includes a network of feed bin assemblies (or feed stations or SSF units) in communication with each other and/or with a central control unit, and each bin assembly is able to sense which animal is approaching or accessing each individual feed bin. In response, the assigned amount of feed material is dispensed to that animal. The SSF unit senses and collects data about the feeding session and about the animal. Data can be handled in any, all, or any combination of the following ways: (1) the data is downloaded to an onboard memory device (e.g., a removable thumb drive or the like); (2) the data is transmitted directly to a local computer where it is processed; (3) the data is downloaded via the Internet or another communication network such as via an Ethernet connection, a cellphone modem, a satellite-based communication device, or any other wired or wireless communication device (note, this data can be periodically downloaded from the SSF units (or the feed system itself) to Internet-based storage, and, from there, the data is accessible for processing or direct observation via Internet-enabled devices); and (4) the data can be directly transmitted to Internet-enabled devices or be transmitted to the cloud. Data from additional sensors attached to each animal or located separately (or both) can also be captured before, after, or in concurrence with feeding session data for synthesizing into data records for each animal of the herd (with such data records archived or stored at the feeding stations and, more commonly, within a database in memory/data storage of the central control unit).

Figure 1:
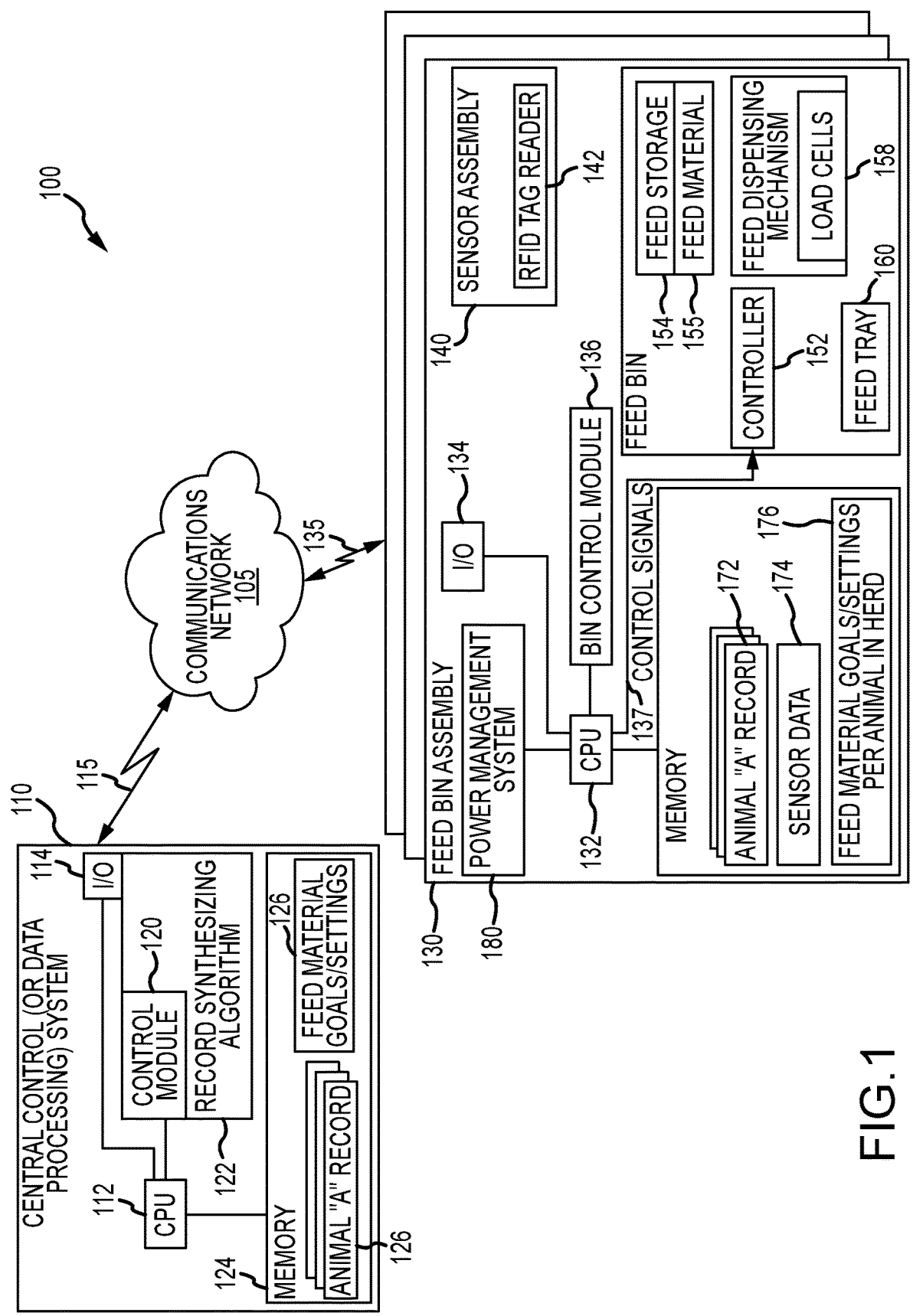
FIG. 1 is a functional block diagram of a feeding system of the present description with a plurality of feed bin assemblies or feed stations useful for feeding individual animals of a herd.

FIG. 1 is a functional block diagram of a feeding system 100 of the present description with a plurality of feed bin assemblies or feed stations 130 useful for feeding individual animals of a herd, which are not shown in FIG. 1 but are understood to be able to access each feed bin assembly 130 when they are positioned for operation (in a pasture or the like). The system 100 includes a central control (or data processing) system 110 that is communicatively linked with each of the feed bin assemblies 130 as shown with wireless signals 115 and 135 over a communications network 105.

The central control system 110 includes a processor 112 managing operations of input/output (I/O) devices 114 such as a transceiver for sending and receiving signals 115, and the I/O devices 114 may also include components of a typical computer system or computing device to facilitate user operations such as a display for displaying a graphical user interface (GUI), a keyboard, a mouse, a touchscreen, and the like. The processor 112 also executes or runs code, instructions, and/of software to provide the functions of a control module 120 to process data in the messages 114 including sensor and/or animal feeding-related data from the feed bin assembly 130.

The control module 120 may include a record synthesizing module/algorithm 122 for generating records 126 stored in memory/data storage 124 for each animal of a herd or each animal accessing the feed bin assembly 130. The memory 124 may also be used to store feed material goals and/or settings 128 for a herd served by the system 100, and these goals/settings 128 may include feed material amounts (e.g., feed and supplements) for each animal in the herd (and/or such settings/goals 128 may be included as a field(s) of each animal record 126). The messages 115 transmitted from the control system 110 to the feed bin assembly 130 may include data from the animal records 126 and/or the feed material goals/settings 128 or data from any or all internal, external animal sensors, and/or environmental sensors (including, for example, animal weight scales) for use in operating the feed bin assembly on an animal-by-animal basis.

As shown in FIG. 1, each feed bin assembly or SSF feeding station 130 includes a computer module that may include a processor 132 and memory 170 managed by the processor 132 to store, in some cases, copies of the animal records 172, sensor data 174 collected by the assembly 130 during animal feeding, and feed material goals/settings per animal in a herd 176 (or this data may be in one or more fields of the record 172), which are received in signals 135 from control system 110 (or may be entered/modified by an operator via I/O devices 134 at the station 130). The feed bin assembly 130 includes I/O devices 134 for communicating over network 105 with the control system 110, and these wireless messages or communications 135 may include transmitting sensor data 174 and/or all or portions of the data stored in each animal record 172 for use in forming and/or updating the animal records 126 at the central location (e.g., an operators office or the like).

The feed bin assembly 130 runs or executes software, code, or instructions to provide the functionality of a bin control module 136, which includes generating control signals 137 for operating a feed bin 150 (e.g., via communications with its controller 152). The control signals 137 may be generated based on processing of the sensor data 174 along with the feed material goals/settings 176 while an animal of a herd is accessing the feed bin 150. The bin assembly 130 includes a sensor assembly 140 providing one or more sensors including, in most cases, an RFID tag reader 142 for reading a tag on the animal to provide data 174 that can be used by the bin control module 136 in identifying the animal accessing the feed bin 150 and, in response, to retrieve feed material goals/settings 176 for that animal 176 and for generating control signals 137 to operate the feed bin 150 via controller 152 to dispense a proper amount and type/mixture of feed material. The bin assembly 130 further includes a power management system 180 for managing power storage and distribution within the assembly 130 (e.g., to the processor 132 and other electronic components such as sensors in the sensor assembly 140 as well as to the feed bin 150 for dispensing feed material).

The feed bin 150 includes a feed storage or store component 154 able to store a predefined volume of feed material 155. The feed bin 150 also includes a feed dispensing mechanism 156 that is configured to respond to control signals from the controller 152 by operating to deliver or dispense a desired amount of the feed material 155 into a feed tray 160 for a particular animal accessing the bin assembly 130 during a particular feeding session. Load cells 158 or other scale components may be included in the feed bin 150 to measure a mass of the feed material 155 being dispensed into the feed tray 160 to provide a more accurate measurement of the feed material 155 provided to the animal, and the load cells 158 may be used to determine the weight dispensed (changes in a weight of the feed storage 154) as well as amount of feed material actually consumed (or at least removed by the animal) from the tray 160 (changes in a weigh of the food tray 160).

As can be seen from FIG. 1, each SSF feed bin assembly or feeding station 130 may include a number of unique components to provide the unique individual animal feeding features of the present description for system 100. Each assembly 130 includes a feed bin 150 with a storage unit 154 capable of holding enough feed and/or supplement and/or mineral, and/or medication (hereinafter referred to as "feed material" or simply "feed") 155 to feed multiple animals a prescribed ration for several days, weeks, or months. The feed bin storage unit 154 can be fabricated panels or walls of metal, plastic or other material that is suitable for the intended purpose (e.g., adequate strength to support the weight of the feed, weather resistance for use outdoors for extended periods/seasons, and the like). The feed bin 150 may be equipped with load cells 158 to monitor the amount of feed 155 in the bin storage 154 to allow the bin control module 136 to calculate the ration of feed material 155 delivered to each animal. To identify each animal, the sensor assembly 140 includes an RFID tag reader 142 that preferably can read the standard half-duplex and/or full-duplex animal ID tags used in the industry. Alternatively, animal recognition technology in sensor assembly 140 could be used to identify individual animals as then approach or access the feed bin 150.

The I/O devices 134 may include a communication module to transmit data from the SSF feeding station 130 to remote users and sites as shown with arrow 135. The communication module of I/O devices 134 can utilize cell modems, ethernet networks, low orbiting satellite modems, or other means to transmit 135 data 172, 174 from the field to specified users (e.g., to subscriber devices not shown in FIG. 1 but well understood in the communications industries) and to a central, permanent archive (e.g., memory 124 of central control system 110 via messages 115 over network 105). The assembly 130 also may include a computer module (e.g., processor 132 providing functions of module 136 and memory 170) to read sensors of assembly 140 including the RFID tag readers 142 and/or other sensors. The computer module is capable of storing in memory 170 many months of data 174 and/or data in records 172, which may be useful when the communication module of the I/O devices 134 is unable to function or to reserve energy. It then can be configured to download automatically when a link is achieved (as shown with arrows 115, 135). Each SFF station 130 may be equipped with a visual display panel in the I/O devices 134 or it can be linked via communications 135 to an application on a smart phone or laptop computer (not shown but may be nearly any portable or desktop client device such as a smartphone, a laptop, a computing pad, or the like) so that data can be viewed and displayed in the field or remotely.

Weight scales or load cells 158 are included within each feed bin assembly 130 so that the weight of feed 155 in the bin 150 or its storage unit 154 is known and logged at any given time (e.g., stored as part of sensor data 174 in memory 170). Each SSF station 130 is linked (as shown via signals 135 and network 105) to an Internet-based data processing and archiving interface 114 of data processing system 110 so that data 172, 174 for each individual animal and/or for the entire herd of animals can be synthesized and displayed to users and producers by the control module 120 using the record synthesizing algorithm 122 to form records 126 for use in creating GUIs in display devices of the I/O unit 114.

Each bin assembly 130 may include a power management unit 180. This unit 180 may include solar panels mounted on a platform in such a way that they can efficiently collect solar energy even at high northern or southern latitudes even in winter. The power management system 180 may also include batteries, battery charging and maintenance circuitry, and peripheral devices necessary to supply power so that each SSF feeding station 130 is able to operate as a self-contained unit and operate efficiently by automatically operating the sensors of assembly 140 and devices (such as the processor 132 and feed dispensing mechanism 156) in such a way to control the power consumption.

Each feed bin assembly 130 may be equipped with at least one of the feed bins or feeding stations 150 (as shown) while other embodiments of the system 100 may have assemblies 130 with multiple feeding stations. Each feed bin 150 includes a feed tray 160 into which the specified amount of feed 155 is delivered, preferably at a rate equal to the consumed rate, by the feed dispensing mechanism 156 from the feed storage unit 154. Each feed bin 150 may also have provisions for or include animal control panels or gates (not shown) so that only one animal can occupy one feeding station/feed bin 150 at a time and may also include adjustable head gates. The animal control panels are removable to facilitate animal training in some embodiments.

The feed dispensing mechanism 156 may take a variety of forms to accurately dispense amounts of the feed material 155 into the feed tray 160 as chosen by the bin control module 136 for an identified animal. In one preferred embodiment, a novel motorized feed auger and hatch mechanism (explained in more detail below) is provided in or as the mechanism 156 for individualized cattle (or other animal) feeding that allows for an inexpensive production of the SSF feeding station 130 relative to its benefits, ease of maintenance and manufacturing, efficient operation, and expandability. The bin control module 136 may be adapted to implement a specialized algorithm to convert volume of feed to mass of feed dispensed, and this algorithm uses a mathematical method and sensor inputs such as those of sensors in assembly 140 and/or those of the load cells 158 (as shown as sensor data 174 in memory 170 in FIG. 1).

With regard to the sensor assembly 140, the bin assembly 130 may be equipped with a global positioning system to identify the location of each assembly 130, and this location information may be stored in data 174 and/or record 172 and/or be transmitted in messages 135 to the control system 110. Weight sensors in assembly 140 (e.g., load cells 158) on the feed bin 150 may be used to determine how full of feed material 135 the feed storage unit 154 is at any given time. Weight sensor data 174 can be transmitted using the communication protocol to central server 110 where the weight of the bins can be tracked, and then a feed truck (not shown) can be dispatched to the precise location of the SSF (when GPS is used, for example) to fill the SSF feeding station 130. Each feeding station 130 can be equipped with additional sensors in assembly 140, such as sensors to monitor metabolic gases (e.g. methane, carbon dioxide, oxygen, hydrogen, aldehydes, ketones, alcohols, and the like). Further, each SSF feeding station 130 may be equipped with a fly-spray system (not shown) for individualized spraying of animals. Additionally, each feeding station 130 can be equipped with readers (in assembly 140) for additional remote or on-cow sensors such as activity monitors, animal temperature, and microphones to monitor respiration sounds when the animal accesses the feed bin 150, and this additional collected data 174 may be transmitted to the central control system 110 in messages 135 and/or store din records 172 for each identified animal.

Each SSF feeding station 130 is linked to an Internet-based data processing and archiving system such as system 110 in FIG. 1. The archiving system continuously monitors each SSF feeding station 130 and notifies users if error conditions occur. Occurrences or error conditions that may trigger notifications/alerts include, but are not limited to: (a) data outside of the operating specifications of each sensor in assembly 140; (b) data that indicates that an animal is not receiving its specified ration; (c) data that indicates that the data link to the internet is not functioning; and (d) data concerning the power status of the SSF feeding station, solar panel, and/or batteries.

The system 100 may include identifiers (not shown but well understood) for each animal of a herd. In some cases, the system 100 utilizes an industry standard RFID ear tag, injected animal ID chip, or neck collar placed on the animal. The RFID devices are preferably half-duplex or full-duplex devices in the frequencies specified in the animal industry for animal identification purposes. Alternatively, the animal identification tag reader 142 used in the SSF station 130 could read non-standard identification tags customized for other animal applications. As shown in FIG. 1, an SSF unit 130 includes a bin storage unit or hopper 154 designed to hold a large quantity of feed or supplement (feed), e.g., feed material 155. Each bin storage unit 154 or an entire housing of an assembly 130 can be mounted on load cells 158 connected to the SSF computer 132 (via controller 152 or directly) so that the contents 155 of the SSF storage unit 154 can be remotely monitored via messages 135 at control system 110 (or at subscribing client devices). The SSF feeding station 130 may be equipped with antennas 142 to receive individual RFID signals to detect the ID of each animal accessing the feed bin 150. Thus, each animal is uniquely identified as it approaches a feeding station 130 within an SSF system 100. An onboard computer 132 running module 136 then identifies the specific feeding instructions (in record 172 or in data 176 in memory 170) for each individual animal and executes those instructions to deliver the user-specified material to each animal via operations of the feed dispensing mechanism 156. Alternatively, a video recognition system in sensor assembly 140 could be used to identify each animal and be linked to the SSF operating system (components 132, 136) to perform the programmed instructions 176.

In some implementations, each SSF feeding station 130 is equipped with multiple feed trays 160, and each feed tray 160 may be considered a separate feeding station in the system 100. Preferably, each tray 160 is equipped with adjustable head gates and/or animal-control gates so that only one animal at a time is able to access material from a feeding tray 160. Alternatively, a headstock that limits one animal at a time to a feed tray may be used. Once an SSF feeding station is occupied, the specified amount of feed by mass is delivered at a rate roughly equal to the animal's feeding rate into the feeding station tray until the animal consumes its ration or leaves the feeding station, whichever comes first. All SSF units and each SSF feeding station are wirelessly networked so that regardless of the SSF unit or SSF feeding station visited each animal will only receive its specified ration of material.

The feeding system 100 also records and tracks and automatically calculates the mass of feed material 155 delivered through a specialized algorithm in module 136 that records weight data using, or obtained, by sensors. It can automatically and precisely determine the mass of daily supplement intake by animal based on sensor data 174 even if the feed density changes. In some applications, sensors in assembly 140 may be placed in each feed tray 160 to determine if there are orts in the feed tray 160 after an animal leaves a feed bin 150. The orts can be automatically attributed to the next animal by a weighing or measurement system (sensor in assembly 140 and/or load cells 158) before and after each visit to the feed tray 160. The SSF feed station delivery rate can be controlled and set at a rate lower than the rate of consumption to minimize the orts if one animal leaves before it consumes its allocated ration. An automated system may be used to monitor the presence of the animal, and sensor feedback processed by module 136 to adjust feed rates in real-time to further minimize orts.

The system 100 also includes several novel design elements that make the feed bin assembly 130 inexpensive to manufacture. By combining several functions into one operation, the number of parts and the labor required to manufacture the SSF assembly 130 are greatly minimized over previous designs. The system 100 can use solar power in each power management system 180 at or on each feed bin assembly 130 so that each can operate autonomously in a pasture, even during the winter in high latitudes. In low sunlight conditions, available solar power can be minimal so the assembly 130 may include special power conserving features. The SSF feeding station 130 can communicate, be controlled, and send data using a cloud-based web interface (provided in or by I/O devices 114 and 134. To send data over the Web/network 105, a cellular or Wi-Fi network can be used. The user can log in, control the system 100 or individual stations 130, drop feed, and then obtain data from the system 100. When the user is in closer proximity to one of the assemblies 130, the user can also communicate with the assembly 130 by connecting to the feeding system 100 wireless network using client device (e.g., a smartphone app or the like). The SSF feeding station 130 is also portable and modular, and, because it is wireless, the SSF feeding station 130 can be easily moved to new locations either by adding wheels to the frame and an attachment tongue or it can be designed to be lifted with a tractor loader.

The volume of the SSF feed storage unit or hopper 154 is preferably large enough to hold enough feed for several animals for at least several days, so the user does not have to travel each day to the site to feed animals, thereby reducing labor. Further, several SSF units 130 can be managed at the same time through the supplied user interface provided by control module 120 and I/O devices 114 of the central control system 110. Rather than controlling the inputs to each SSF feeding station 130, the user can control the amount of feed by animal via goals/settings 128 and/or by updating fields in animal records 126 and then the central server 110 communicates (as shown with signals 115 and 135) with the SSF feeding stations 130 to set the amount of feed material 155 dispensed from each feed tray 160. Because total bin weight data is logged by the system 100 as part of sensor data 174, a multiple feeder user network/system 100 can be developed so that users or feed suppliers can monitor the amount of feed 155 in several feed bin assemblies 130 at one time from one central location (e.g., via I/O 114 in central control system 110 or via client devices subscribing to messages 115 or 135), and feed trucks can be automatically dispatched by signals/message 115 or the like to refill each SSF feeding station 130 when the feed hoppers/storage units 154 are low on feed material 155. A GPS system in sensor assembly 140 can be placed in each feed bin assembly 130, and the GPS location data (part of sensor data 174) can be transmitted back to the central server 110, so that even when feed bin assemblies 130 are moved, the feed truck operator can easily locate each SSF to fill the bin.

With the features and operations of the feeding system 100 understood, it may now be appropriate to discuss prior approaches and technologies so as to describe differences between these and those implemented with system 100. Individualized computerized concentrate feeding systems have been used for many years in dairy environments. In typical operations of these systems, there is a feeding stall with a box containing the computerized system and sensors built into the stall. The animal with an identification tag attached approaches the feeder, then a pre-programmed amount of feed is dispensed to each animal. Some systems aggregate this data from several feeders and then control the total amount of feed for the units. The feeders either have a feed-bin to store feed or a central feed bin and dispatching system to store large quantities of feed. In these systems, a distribution system supplies feed to each bin.

The limitations of these systems include that they are not suitable for pasture environments because they are not portable. They are also expensive to manufacture because each feed bin must have at least one control motor to dispense the feed, independent wiring, and other sensing mechanisms. Additionally, the power requirements of these systems are high. Therefore, in a pasture environment where solar power may be limited, the power design requirements are too high to be feasible, especially in high northern and southern latitudes during winter. Because these systems are not portable, they do not include GPS devices to track the location for easy refilling. Because they have independent feed dispensers and motors, they use controls to dispense feed based only on the amount of rotations or volume dispensed from each feeding station. Often, these feeding systems are controllable through a central online interface.

In other applications, portable cattle feeders with feed bins and dispensing mechanisms are used in pasture, but they either are free-choice and offer no automated control of the feed. In cases where they include electronic feed mechanisms, they are operated using a set timer system so they will turn on and dispense feed, but there is no individual animal control of feed dispensing, identification, or measurement considerations. No other systems to the present time utilize, nor are they capable of reading on-board cattle sensors or independent metabolic gas sensors.

In another example, a portable system has been developed that includes a feed bin, and four feed stations are built into the feed bin. It includes a solar panel and data transmission capabilities so the data can be transmitted to the cloud, and the system can be controlled using a web interface. Local data connections can be made to the system and controlled through a web application. The system controls the amount of feed dispensed to each animal using RFID technology through user-set controls, and it is portable. However, it suffers some critical design flaws. First, the system does not include any weight sensing devices either in the primary feed bin or in the feed trays. Often, users will need to use highly variable (by density) feed materials. Because the system does not include load cells, the computer cannot automatically determine the mass of feed supplied to each animal with any accuracy as it only dispenses feed by volume. Also, in contrast to the present system and its operations, these prior portable systems cannot determine the amount of feed in the bin to inform operators when refilling is required. In addition, they do not use GPS so that feed truck operators can know where to refill the bin.

Further, in such designs, the feeder system has one large bin for dispensing feed to separate feed stations. Each feed station has its own auger and motor systems to dispense feed to that station. Therefore, each feed station requires expensive motors, augers, and high current wiring to operate each motor independently, which greatly increases production costs. The motors are also located inconveniently inside the bin where they are difficult to access for maintenance or replacement. It is difficult to expand the system to more feed openings, and the feeder configuration is difficult to change. Each unit always has a set number of openings (four), and these feeder systems cannot be easily and inexpensively manufactured with more openings to accommodate additional animals. The prior feeder systems do not have any special features to control and minimize power consumption on pastures to allow it to operate in high latitudes. Such systems also do not have any provisions to precisely measure interference by other animals in the event that an animal leaves early and another animal obtains the last animal's feed. Further, the solar panels cannot be tilted to maximize electricity production in high latitudes.

Figure 2:
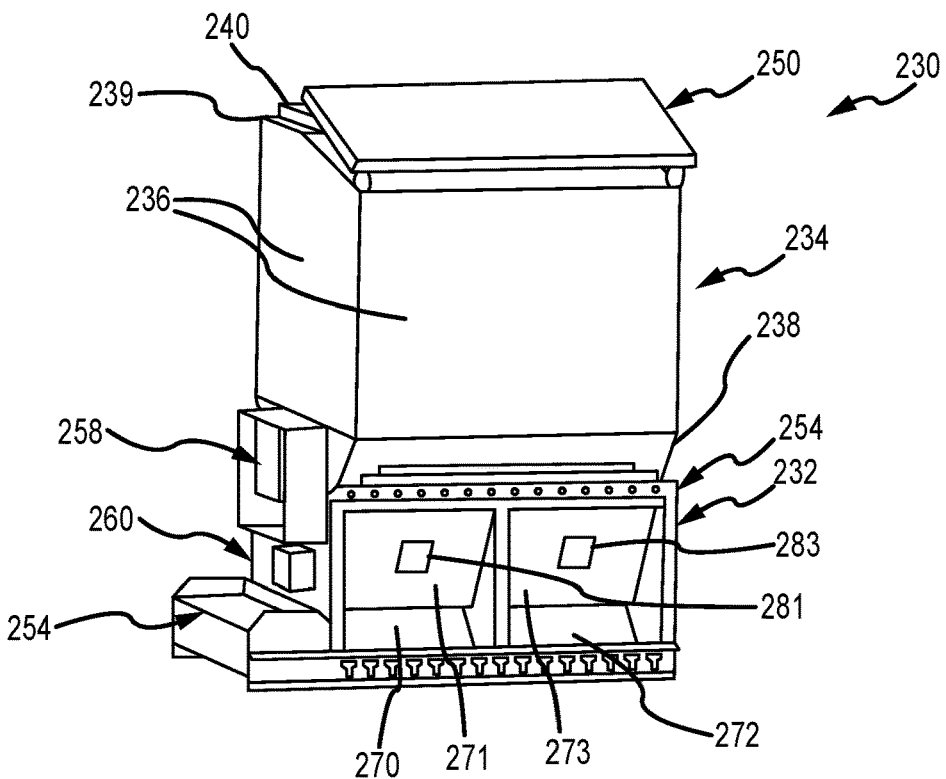
FIG. 2 is a front perspective view of a feed bin assembly or feed station of the present description that may be used in the feeding system of FIG. 1.
Figure 3:
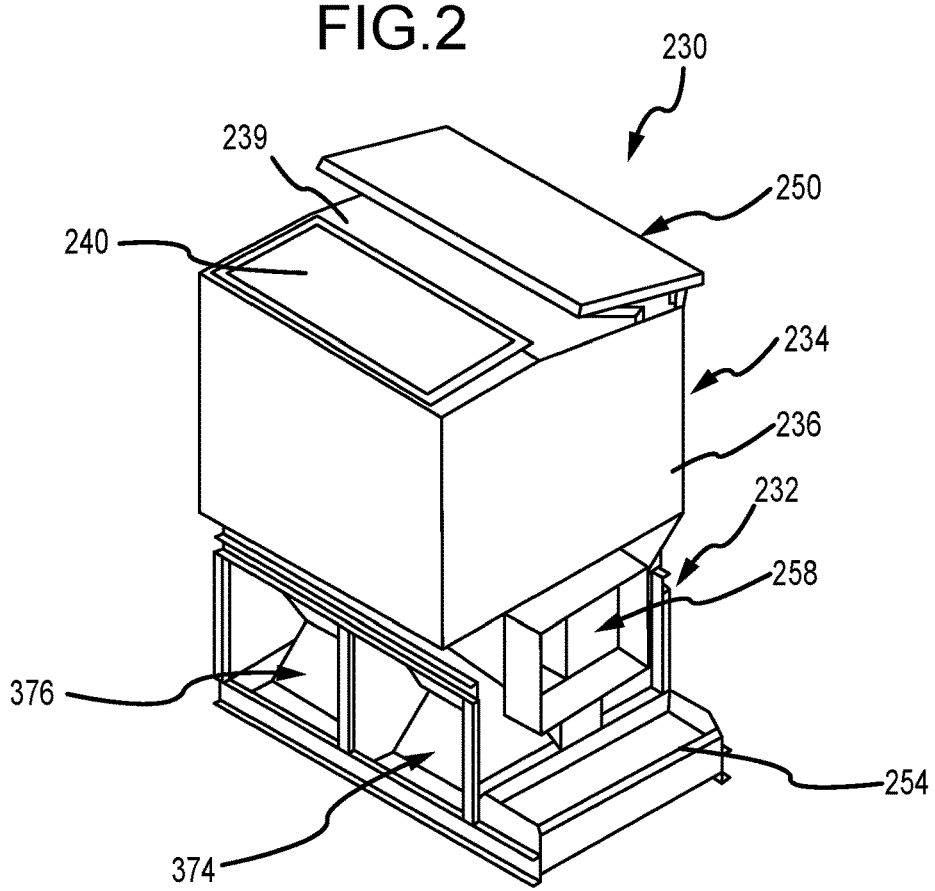
FIG. 3 is a rear perspective view of the feed bin assembly of FIG. 2.
Figure 6A:
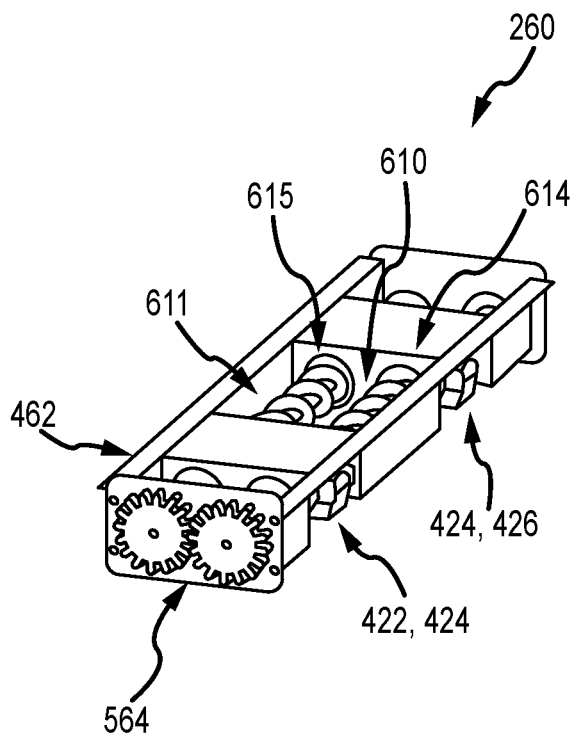
FIGS. 6A-6C are a top perspective view, a top view, and a bottom view of the feed dispensing mechanism of the feed bin assembly of FIGS. 2-5.
Figure 6B:
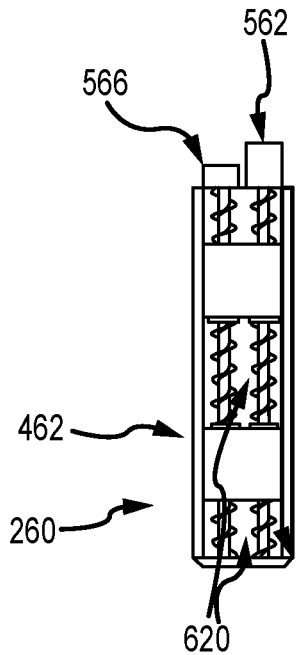
Figure 6C:
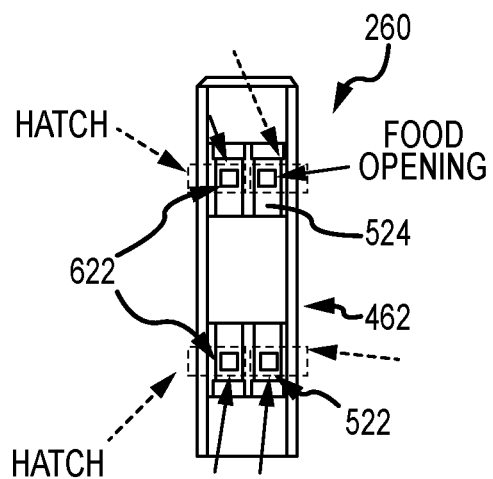

At this point in the description, it may be useful to discuss one useful implementation of a feed bin assembly or feeding station as may be used for component 130 of the system 100 of FIG. 1. Particularly, FIG. 2 is a front perspective view of a feed bin assembly or feeding station 230 of the present description that may be used in the feeding system 100 of FIG. 1. FIG. 3 is a rear perspective view of the feed bin assembly 230 of FIG. 2. FIG. 4 is an enlarged view of the lower portion of the feed bin assembly 230 of FIG. 2 during operations with feed tray doors or covers 271, 273 over the front two feed trays 270, 272 being lifted to expose feed hatches 422, 424. FIG. 5 is rear partial and enlarged perspective view of the feed bin assembly 230 of FIGS. 2-4 showing features of the feed dispensing mechanism 260. FIGS. 6A-6C are a top perspective view, a top view, and a bottom view of the feed dispensing mechanism 260 of the feed bin assembly 230 of FIGS. 2-5.

As seen in FIGS. 2 and 3, the feed bin assembly 230 includes a feed storage unit or hopper 234 formed of four vertical sidewalls 236, a top cover 239, and a lower portion 238 of the body of the hopper 234, and the hopper 234 is supported upon a lower housing or support element 232. A feed bin lid 240 is provided in the top cover 239 to allow access to the inner volume to add feed material. A solar panel 250 is shown to be mounted on the other side of the top cover 239 to convert solar energy into electrical power that is used via batteries 254 mounted on one end of the lower housing 232. A weigh scale (or similar sensor(s)) 254 is provided between the hopper 234 and the lower housing to sense a weight of the hopper and any feed material contained therein. A computer module is provided on the bin assembly 230, with FIG. 2 showing a control display panel 258 for this computer module, and, as discussed for FIG. 1, the display panel 258 may be used to display the present weight measured by the weigh scale 254 (as well as calculated feed material weight) while the computer module provides wireless communication of sensor and other data to a central control system and/or to subscribing client devices.

The lower housing 232 is configured to provide four feed trays 270, 272, 374, 376 (e.g., two front trays 270, 272 and to rear rays 374, 376) to allow four separate animals to concurrently access the feed bin assembly 230 to feed. A feed dispensing mechanism or assembly 260 is provided to selectively dispense particular amounts to each tray 270, 270, 374, 376 based on which animal is determined to be accessing it and typically as measured by mass rather than only volume. Covers or doors 271, 273 cover the dispensing mechanism 260 near trays 270, 272 and support RFID tag readers or antennae 281, 283 for reading ear tags (or other identifiers) of animals accessing trays 270, 272. This identifying information for each animal is processed by the computer module on the bin assembly 230, and, when an animal that is allowed access to the bin assembly 230 is identified, the covers or doors 271, 273 may be independently lifted as shown in FIG. 4.

FIGS. 4 and 5 also show a drive housing 462 of the dispensing mechanism/assembly 260, and this housing 462 is used to mount the mechanism/assembly 260 within the bottom portion 238 of the body of the hopper 234. The housing 462 houses a pair of drive augers (seen at 610, 611 in FIG. 6A), which are driven to rotate about their longitudinal axes by an auger motor 562. Rotation of augers by motor 562 is measured or sensed by an auger sensor 566, and a gear set 564 is provided between the output of motor 562 and an input or drive portion of the auger to control the rotation of the augers (e.g., for opposite rotation of the augers). Feed hatches 422, 424, 522, 524 are provide adjacent (or above) the trays 270, 272, 374, 376, respectively, to control dispensing of feed material from the hopper 234 into each tray 270, 272, 374, 376, with separately operable actuators for each hatch (e.g., see actuators 425, 426 for hatches 422, 424, respectively, in FIG. 4). FIGS. 4 and 5 also show that the feed bin assembly 230 may include an activity sensor 440 in the sensor assembly, and the weigh scale 254 may include feed bin load cells 570.

FIGS. 6A-6C illustrate additional details of the feed dispensing mechanism 260 including showing the arrangement of a pair of side-by-side augers 610, 611 within the housing 462. These figures also show the arrangement of the gear drive 64 for reverse rotation of the augers 610, 611 as well as the location of the drive motor 562 and rotation sensor 566 external to the housing 462. As shown, the feed hatch and associated actuators 422, 424 and 425, 426 are mounted to the housing 462 with two per side (or four total in this example). These are positioned below feed tubes 614, 615 through which an auger 610 or 611 extends. Upper openings 620 for feed from the hopper body lower portion 238 are provided in the housing 462 between the tubes 614, 615 to define passageways for feed material during dispensing operations. Further, in this regard, bottom feed openings 622 are provided to define passageways for feed material out of the feed tubes 614, 615 such that feed material drops by gravity to a food tray when feed hatches are open or moved from the openings 622 by actuators (as shown in FIG. 6C for feed hatches 522, 524). Note, while FIG. 6 shows use of an alleyway to control animal access, an adjustable head gate is used in some preferred embodiments to restrict one animal using the system.

The new technology described herein provides, with feed bin assembly 230, an animal feeder that holds a large quantity of feed in a common feed bin or feed storage unit/hopper 234. Preferably, the bin or hopper 234 provides the feed, supplement, mineral and/or the medicinal requirements (feed material) for several animals for at least several days. The lid 240 of the bin or hopper 234 is removable to facilitate easy filling. On the top 239 of the bin or hopper 234, there can be a solar panel 250 to provide power for SSF unit or assembly 230 on a pasture where there is no power available. The solar panel angle is adjustable to provide optimal solar power in the winter when the sun angle is low in high latitudes. The solar panel 250 provides power to batteries 254 in or near the base 232 of the feed bin assembly 230, where there can be a charge controller (not shown) to charge the batteries 254 or, optionally, a DC-AC converter so the unit 230 can run from an AC power source. In some situations, it might be advantageous to recharge the batteries 254 with an independent generator or a generator that is linked to the SSF controller (which includes display panel 258).

The bin or hopper 234, at the base of the SSF assembly 230, funnels down via the hopper body's lower portion 238 into one common feed mechanism, which is located at the bottom of the feed bin 230 (e.g., in lower housing 232. This allows loose feeds, such as feed pellets, to flow under gravity into the feed dispensing mechanism 260. The feed dispensing mechanism 260 is an auger system (see augers 610, 611 in FIG. 6A) with openings 620 in the top of dispenser housing 462 that allow the pelleted feed to flow from the bin or hopper 234 into the augers 610, 611 at defined intervals along their lengths. The auger-based feed dispensing system 260 includes two augers 610, 611 running the length of the feed bin 232 in housing 462, near the bottom of the bin body's lower portion 238. During feed or dispensing operations, each auger 610 and 611 turns in a direction opposite to the adjacent auger 611 and 610. The opposed rotation is accomplished using a gear transfer 564 located on the protruding end of housing 462, outside of the feed bin/hopper 234, of each auger shaft. Alternatively, the reverse rotation could be accomplished by attaching a motor to each shaft and turning both motors on and off at roughly the same interval. The opposing auger rotation allows the feed to circulate inside the bin or hopper 234 without accumulating only at one side of the bin or hopper 234. On both ends of the augers 610, 611, the inside of the hopper body's lower portion 238 is shaped to facilitate feed pushed by the augers 610, 611 to recirculate back to maintain uniform bin levels across the length and width of the bin or hopper 234.

The augers 610, 611, at specified locations along their lengths, are enclosed into a tight-fitting tube 614, 615 surrounding the augers 610, 611, respectively. There is a small opening (usually rectangular) in the bottom of the tube 614, 615 (see FIG. 6C for openings 622 in tube 615). The feed tubes 614, 615 are preferably long enough to obstruct the flow of feed from the bin 234 out of the small opening 622 when the augers 610, 611 are stationary. The SSF feeding station 230 is designed so that feed only flows through each opening 622 into each feed tray 270, 272, 374, 376 when the augers 610, 611 are turning. A retractable hatch 422, 424, 522, 524 covers each opening 622 in the feed tube (pipe) 614, 615 so that feed only flows through the opening 622 into the feed tray 270, 272, 374, or 376 when the augers 610, 611 are turning and the feed hatch 422, 424, 522, or 524 in the feed tube 614 or 615 is retracted. Each feed hatch 422, 424, 522, and 524 includes an actuator (see actuators 425, 426 in FIG. 4 for hatches 422, 424), usually an electric linear actuator that is controlled by a controller that is linked to the onboard computer module. Commands from the computer module open and close the hatch.

Figure 7:
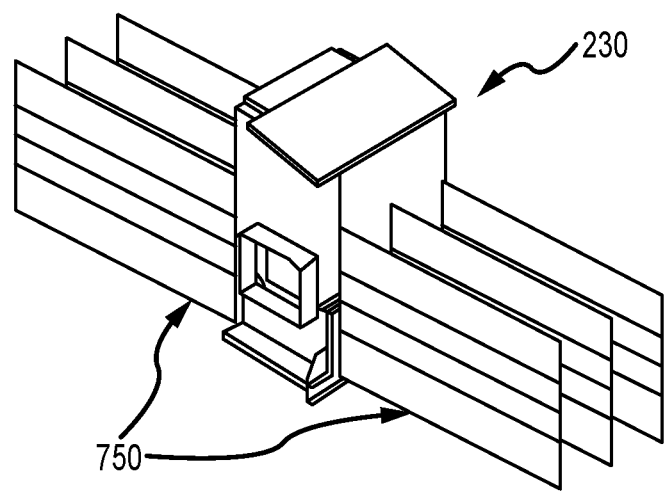
FIG. 7 shows the feed bin assembly of FIGS. 2-6C with the addition of an alleyway system limiting access to each feed tray to a single animal.

A sensor 566 linked to the feed augers 610, 611 counts auger rotations. By controlling the duration that the feed hatch is open and the auger rotations, the computer module is able to control the specified amount of material to drop out of the bottom of the feed bin 232 into one of the feed trays 270, 272, 374, 376. The feed pipe/tubes 614, 615 normally have four feed hatches. However, the number of openings is only limited by the required space between feed hatches and the length of the feed pipe/tube 614, 615; therefore, in some configurations, many feed hatches and openings can be accommodated. So, if there are four openings, there are four separate feed trays, and only one animal can access each feed tray at any given time. Such animal access control may be provided as shown in FIG. 7 with the addition of alleyway control gates 750 defining lanes with widths matching that of the feed trays and/or a small amount greater than a largest animal to be fed.

During the operation of the SSF feeding station 230, the feed drops from the feed bin 234 though the feed hatch opening 622 when the feed hatch 422, 424, 522, 524 is opened into the feed tray 270, 272, 374, 376. The initial drop of feed when the hatch 422, 424, 522, 524 is opened is larger than subsequent drops. After the initial feed drop, if the augers 610, 611 are rotating at the same time as the hatch 422, 424, 522, 524 is opened, feed will continue to drop out of the opening 622 into the feed tray 270, 272, 374, 376 at a rate proportional to the rate that the augers 610, 611 turn. By controlling the rate at which the augers 610, 611 rotate, and the opening and closing of the feed hatch 422, 424, 522, 524, the feed rate can be repeatably controlled. When the feed hatch 422, 424, 522, 524 is closed, a flexible seal (usually rubber) in the hatch opening 622 prevents feed from dropping into the feed tray 270, 272, 374, 376, even if the augers 610, 611 are rotating. This feature allows feed to drop out of specific openings 622 according to animals that visit specific feed trays 270, 272, 374, 376. Thus, if an animal were only to visit one feed tray 270, 272, 374, 376 to receive feed, the hatch 422, 424, 522, 524 for that feed tray 270, 272, 374, 376 is opened, but the other feed hatches 422, 424, 522, 524 would remain closed. Therefore, feed would only drop out of the hatch 422, 424, 522, 524 that was opened when the augers 610, 611 were spinning. At the same time, if all openings 622 are simultaneously visited by eligible animals, all of the feed hatches 422, 424, 522, 524 will be opened, and the feed will flow for all animals when the augers 610, 611 rotate.

Usually, only one or at the most two larger motors 562 are required to operate the feed augers 610, 611. Having fewer large motors, reduces costs of the system 230 and also reduces power consumption. Often, the large motor 562 is brushless, which significantly reduces the power consumption. Each SSF feeding station 230 includes a rotation sensor 566 on the auger(s) 610, 611 to monitor and control the rotational rate of the augers 610, 611 during operation of the feed dispensing mechanism 260. The sensor 566 could include an electronic rotary encoder or a magnetic Hall sensor system. Only one rotation sensor 566 is required per large motor 562, and, often, the sensor 566 is located on the auger shaft. In some cases, the computer module on assembly 230 might give a command for the augers 610, 611 to reverse rotation for a specified number of turns in order to attempt to clear a jam caused for example by a clump of feed. Because there are only one or two large motors 562 and equivalent number of sensors 566, manufacturing costs are further reduced for the assembly 230.

Located adjacent to each feed tray is an sensing antenna (see antenna 271 for tray 270 and antenna 273 for tray 272 in FIG. 2, for example) to read the electronic ear tag (usually an RFID tag) of an approaching animal. The computer module processes this ID information and then gives instructions so that the user-defined amount of feed is dispensed for that specific animal in the tray associated with the antenna/RFID tag reader. The antenna connects to a control panel electronic tag reading system of the control module in some implementations of assembly 230 and/or information is transmitted to a computer controller (associated with display panel 258) that is located on the SSF feed station 230. The controller and computer may communicate via wireless connection to a cloud-based server system (as shown in FIG. 1 in system 100 to central control system 110) to receive information about the amount of feed to be dispensed to each animal, depending on the amount of feed already consumed by that animal in any SSF feeding station 230.

Located near or on the feed bin assembly 230, are one or more low power sensors 440, such as an inferred sensor, to determine if there are animals adjacent to or near to the feed bin. If animals are not near the feed bin assembly 230, the assembly's controller/computer module automatically turns off some or all of the non-essential devices and sensors that consume power. For example, the controller and/or RFID antenna are turned off, as are the wireless communication system and the feed motors. At this time, the SSF feed station 230 is in sleep mode with minimal power consumption. When an animal approaches the feeder and is sensed by activity sensor 440, the computer module will wake up and turn on the RFID antenna and all other sensors and functions, so that normal feeding can occur. The feed bin assembly 230 may be also configured with software on its control or computer module to control the wireless link and power consumption so that the required communication with the server occurs. This will significantly reduce power consumption so that the SSF feeding station 230 can function better in winter and low-solar power environments.

Optionally, there is at least one weighing device 254 that is placed on the feeder bin assembly 230. In one application, the weighing device 254 includes four load sensing cells 570 where one cell is placed on each corner of the feed bin hopper 234. In another, a low friction hinge could be used at one end of the feed bin, and then one or two load cells 570 could be place at the other end of the bin. Using a hinge and fewer load cells method is less precise but costs less. The load cells 570 are used to weigh amount of feed in the bin or hopper 234, and the computer module/controller of the assembly 230 continuously logs (e.g., with one second resolution) the mass of feed in the bin or hopper 234.

The system's controller or computer module may, in some cases, implement or use an algorithm to accurately determine the mass amount of feed dispensed to each animal over time. For example, when a hatch is opened, a volume of feed is immediately dropped, which is equivalent to the enclosed volume of the inner diameter of the auger tube occupied by the feed. When the auger is on and the hatch is opened for a specific tray, additional pellets will enter the auger and feed out at a given rate proportional to the rate at which the motor rotates the auger. The feed rate of pellets is linearly proportional to the rotation rate measured by the auger sensor. Therefore, the volumetric amount of feed fed for any given animal visit to the feeder is equal to the initial mass by volume dropped when the hatch is opened plus the rate of auger rotation multiplied by the volume per unit rotation multiplied by the amount of time the hatch is kept open. The volumes are defined by the dimensions of the auger tube and are usually the same for each opening and the same regardless of feed type.

To dispense more feed to one animal, the hatch can be kept open and the auger turned on for a longer period of time during an animal visit. To stop dispensing feed to an animal, the hatch can be closed for that feed tray by activating the actuator for that hatch. Also, of significance, there can be a low-cost sensor on the hatch to document the position of the feed hatch on a secondly basis, and this position can be continuously recorded by the feed bin assembly's computer system. The sensor can be a Hall sensor or an electrical contact sensor or a digital encoder.

In some cases, the entire feed bin or hopper (element 234 in FIG. 2) is mounted on load cells; therefore, the mass of the feed inside the bin is known and can be logged continuously. Also, the number of hatch openings and closings, along with the auger rotation time and speed while the hatch is open, can be logged by the control computer on a secondly basis. It can be important that the auger, because there are only one or two motors, be turned on anytime a hatch is open to dispense feed in any feed tray.

An algorithm can be used to convert the known volume dispensed to an animal to a precise estimate of the mass dispensed. The algorithm uses the following technique. A selected start and end time period is specified, usually for a period of one day (e.g., midnight to midnight), but this period could be increased or decreased and is somewhat arbitrary. For a start time, the mass of the bin is determined from the secondly logged bin mass sensor data. Then, from the start time to the end time, the numbers of hatch opening volumes are summed for all feed trays within the given time frame. Also, with the time period, the amount of auger rotation and the volume dispensed is summed only when the hatch is open for that feed tray. Then, this time is summed for all feed trays.

Next, the total volume dispensed between the start and end time can be determined by summing the hatch open volume and the rotation volume. Then, the average density of the feed is determined by dividing the total volume by the total mass to determine a very accurate averaged calculation of the feed density within the selected time period. Finally, to determine the feed mass dispensed to each animal, the sum of hatch opening volume plus the sum of rotation volume for a feed tray, when that animal visited that feed tray, is multiplied by the determined feed density.

The calculated feed density is then used to adjust the feeding operation by the onboard computer module (or the central control system). For example, if an animal were to receive 1 kg of feed and one hatch open event is determined to drop 100 grams of feed, and the auger dropped 100 grams of feed per minute, during the visit. To deliver the specified 1 kg of feed to that animal, the auger would need to be rotated at the same speed for nine more minutes.

Usually, the feed rate into the tray is set, e.g., automatically by the computer (for example using sensor data) at a similar rate as the feeding rate of the animal. If the feed rate is too fast, more feed can accumulate in the tray than eaten by the animal, and, if that animal were to leave early, left over feed from that animal could be eaten by the next animal and that animal could receive more feed than expected. Therefore, optionally, each feed tray can include a weighing or sensing device, such as an optical sensor or a camera, to measure the amount of feed in the feed tray. Normally, the sensing device is a load cell, but a volumetric measurement sensor could be used to determine tray feed mass because the feed density is known. The feed tray data is also usually logged by the control computer on a secondly basis. The amount of feed in the tray just before a visit and then the amount of feed in the tray after a visit can be determined using the second by second feed tray mass data. The mass of feed eaten is the difference between the mass of the feed before the visit and after the visit plus the amount of feed dispensed during the visit. This allows for leftover feed to be tracked over time and to be adjusted for each animal, either automatically by the computer or by the human operator.

Data and information captured by the control computer is periodically sent to a central server using an Internet connection that is usually wireless. The wireless data transfer can use Wi-Fi, a cellular modem, a laser data system, a satellite modem, or the like. The user can log into the feeder using a username and password and change the feeding amounts by day or week or even by the hour for all animals or for specific animals. In addition, the user can review the animal intake mass by animal. The user can also review any of the secondly raw data or the aggregated data. The user can also review how much feed is remaining in the feed bin. Usually, the feeding data is aggregated by user, rather than by feeder, because the user may have multiple feeders, sometimes in a common location. The feeding data is aggregated to the central server, and then the server sends to each feeder system the amount of feed remaining in case an animal visits a different unit. So, rather than set the amount of feed by feeder, the user sets the amount of feed for each animal, and the units can communicate with the central server to determine the correct amount of feed dispensed by each feeding station.

However, if there is no wireless connection, or even if there is a wireless connection, the user can download an app onto their smartphone or a portable computer, so that when the user is in close proximity to the unit, the user can connect to it wirelessly, e.g., using Bluetooth. That way, users can review data, download data onto their cellular phone, control feeding amounts, and review which animal are using the system. The downloaded data then can be uploaded to the central server at a later time when the user's computer or smartphone has an Internet connection.

Figure 8:
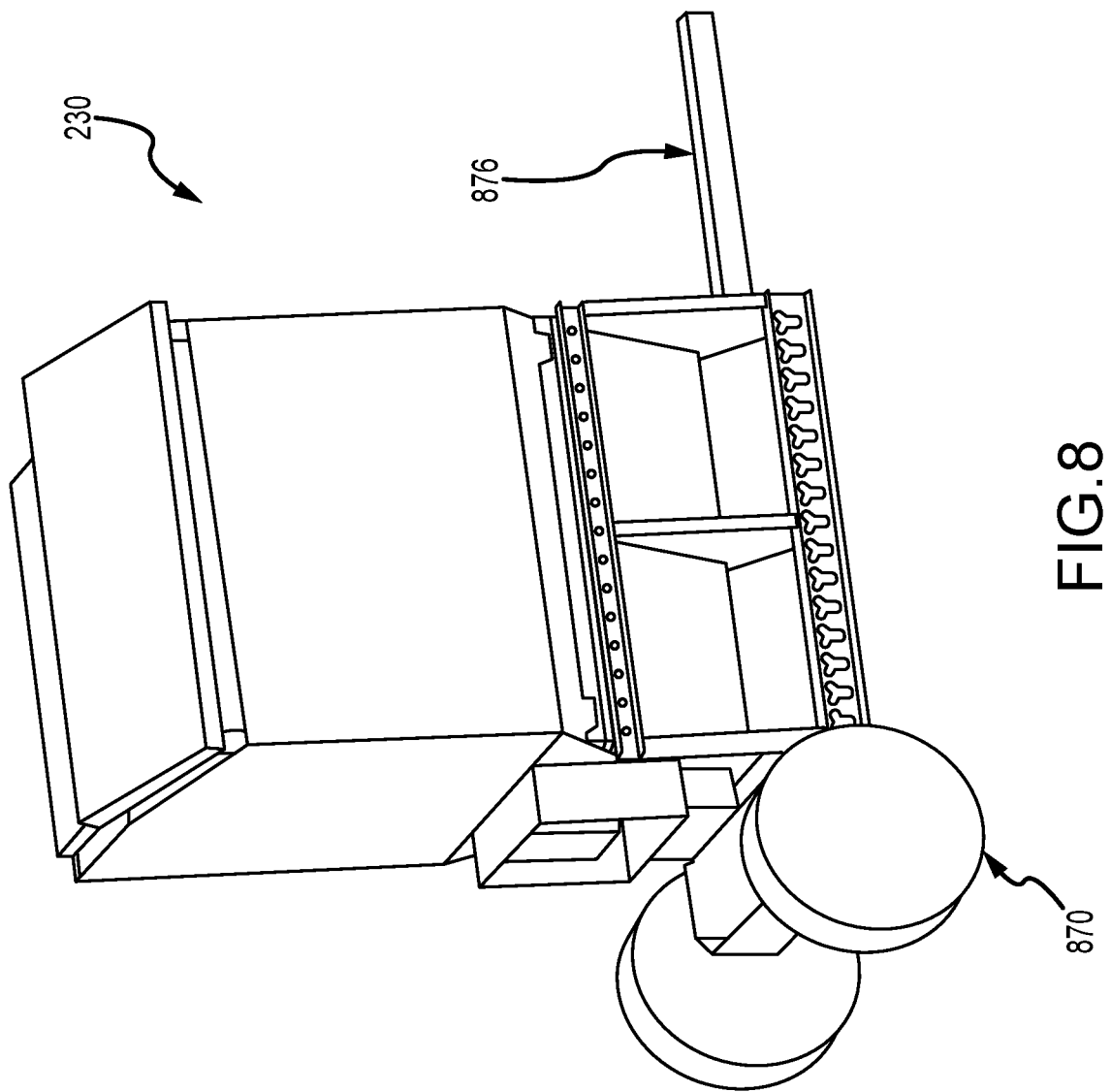
FIG. 8 illustrates the feed bin assembly of FIGS. 2-6C modified to provide enhanced portability for movement throughout an operator's property to feed a herd.

The feeder computer and control system also may have a GPS system to identify the location of the SSF at any given time. The feed bin mass and GPS data are also of importance to determine how much feed is remaining in the feeding system at any given time. This data can be aggregated and reviewed for several feeders through the web interface. The user, or potentially a feed supplier, can login and review how much feed is in the bin, along with current feeder location, and then can dispatch feed trucks to the exact location to fill the bins. That way, if the feeder is moved regularly, the feed truck operator can drive directly to the feed bin to fill the feeder system. The feeder system can be portable; and can be lifted and moved by a machine, such as a tractor. Optionally, as shown in FIG. 8, the feed bin assembly 230 can be equipped with optional farm implement wheels 870 and moved with a tractor (not shown) via towing tongue/connector 876 attached opposite the wheels 870.

Other sensors may be included as part of the feed bin assembly 230 such as methane and carbon dioxide sensors to measure breath concentrations (such as non-dispersive infrared), temperature scanners, or cameras that could scan eye condition. The SSF feeding station 230 can also be equipped with auxiliary readers to download onboard (or off board/off animal) cattle sensor data such as data from activity monitors, temperature monitors, activity tags, or breath sensors (which may be provided in or near the feed tray(s) of the feed bin assembly 230 to measure breath concentrations). These sensors could be used be used to identify animal health problems. Additionally, the feed bin assembly 230 could be equipped with a fly spray system.

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as hereinafter claimed.

In some implementations, the new feed system used and operated to provide pasture improvement and pasture management. In this regard, one important goal of grazing systems is to attain a uniform utilization of forage species across a pasture area. If the pasture area is large with respect to the number of animals, the animals will tend to be selective and focus their consumption on highly palatable "ice cream" plants and ignore plants which are less palatable. The result is that the palatable, often very nutritious, plants are over-utilized, and the pasture becomes degraded and overgrown with less-desirable forage.

An alternative strategy has been to concentrate a relatively large number of animals in an area that is small enough so that each animal cannot be selective and still become satiated. In these systems, all vegetation is grazed once, and the animals are moved on. Vegetation is only grazed once thereby minimizing overutilization of ice-cream plants, soil compaction, and local pollution. Over time, desirable, grazing-tolerant plants tend to thrive and less tolerant noxious weeds and invasive species can be minimized through more concentrated grazing in affected areas. As a consequence, soil carbon accumulates thereby increasing pasture fertility and sustainability. This soil conservation, sustainability function will become more important in the future. The NRCS could, for example, pay for the SSF for farmers who use them to decrease runoff (e.g., improve water quality) and increase carbon sequestration to offset GHG production. Obtaining high intensity short duration grazing creates many benefits for producers, but, in large pastures, it can be difficult to obtain. Dividing large pastures into small paddocks of appropriate size for the herd is effective but expensive. Without fencing to subdivide large pastures into manageable paddocks, animals tend to overgraze in proximity to water. In some cases, where extensive fencing is impractical, portable water supplies are moved to various parts of the pasture to achieve results similar to those of fencing without the expense and labor of herding animals to new paddocks every few days. The results are similar to those achievable by fencing. Almost all plants get grazed.

To meet these goals, the new feed system can be used to achieve similar results. Animals will soon become "imprinted" on the feed system. They will learn that it dispenses "treats" (similar to ice cream plants), and an inevitable consequence is that animal grazing behavior will tend to be more intense and less selective in the proximity of the feed system or its feed bin assemblies. By moving, the feed bin assembly(ies) around in large pastures, short duration intensive grazing can be achieved without the expense of fencing and without the labor required to move animal herds manually at short intervals. Ranchers could potentially gain carbon credits employing the feed system in this way. Increasing soil carbon will also result in decreased runoff and decreased soil erosion. In addition, by locating a feed bin assembly(ies) of the feed system near invasive species, the expansion might be more effectively controlled.

It should also be understood that the computing/RFID system employed by the feed system can be used to read other sensors on the market now and those that will be developed later. For example, ruminant sensors and activity monitors are sometimes used in the dairy industry to identify sick and/or lame animals. The feed systems described herein can be configured to incorporate the appropriate readers so that when these animals visit a system's feed bin assembly, data are downloaded and later transmitted to the feed system's central server(s).

Further, the combination of sensors incorporated into the feed system (e.g., at each feed bin assembly of the feed system) plus those that are independent from the feed bin assemblies can be used to automate the dispensing of feed or minerals or medicines. For example, a user of the feed system feed bin assemblies may make use of a scale (or scale-based assembly) that weighs the front half of an animal when they get a drink of water. Algorithms may be implemented, as part of the new feed system or to be run externally, that can accurately predict whole animal weight based on the front-end weight. The advantage of this system over weighing an entire animal is that animals are reluctant to step into a shaky apparatus with all four feet, but they are willing to step up on a low platform with their hind feet firmly on the ground in order to get a drink.

The scale-based assembly with its predictive algorithms can be configured to transmit weight data to the central data processors of the feed system where the data can be processed further into weight gain data, which is then used to automatically adjust the rations dispensed by the feed system. This data can also be used to detect reduced rate of gain of the herd when it is time to move the feed bin assembly (ies) and cattle to a new paddock or to a new portion of a large pasture. The data can be converted to "pasture yield" for each gridded segment of a pasture and then applied to precision pasture treatments such as reseeding, fertilization, and weed control. A unique feature to be recognized is that the feed system can potentially read and assimilate data from both internal and external sensors, and the data can be processed at a central facility where the results are synthesized and used in a manual or in an automated way to adjust pasture treatments and animal handling via operations of the feed bin assemblies described herein.

We claim:

1. An apparatus for dispensing feed material to individual animals of a herd, comprising:
   a feed hopper with body having a first opening for receiving the feed material into an inner space of the body and having a second opening in a lower portion of the body for discharging the feed material from the inner space of the body;
   a lower support structure supporting the feed hopper;
   a feed tray in the lower support structure;
   a feed dispensing mechanism operable to selectively dispense the feed material from the feed hopper into the feed tray via the second opening in the body;
   a sensor assembly sensing data for an animal in the herd accessing the feed tray; and
   a controller processing the data sensed by the sensor assembly to determine an identity of the animal and, in response, to first retrieve based on the identity a predefined mass of the feed material assigned to the animal and to second operate the feed dispensing mechanism to dispense into the feed tray a volume of the feed material determined to provide the predefined mass
   wherein the sensor assembly includes a GPS-based locating device determining a location of the apparatus and wherein the controller wirelessly communicates the location to a remote device to facilitate refilling the feed hopper with the feed material.

2. The apparatus of claim 1, wherein the sensor assembly includes a weight sensing device for determining a weight of the feed hopper and wherein changes in the weight of the feed hopper are used by the controller to control the feed dispensing mechanism to dispense the volume of the feed material or the weight is communicated to a remote device to facilitate refilling the feed hopper with the feed material.

3. The apparatus of claim 1, wherein the sensor assembly includes a weight sensing device for determining a weight of the feed tray and wherein the controller uses the weight of the feed tray prior to the animal accessing of the feed tray to determine a remaining amount of the feed material and to reduce the volume of the feed material dispensed based on the remaining amount.

4. The apparatus of claim 1, wherein the feed dispensing mechanism comprises an auger extending horizontally within the lower portion of the body or within the lower support structure to move and distribute the feed material over the second opening and any additional openings provided for discharging the feed material from the feed hopper.

5. The apparatus of claim 1, wherein the feed dispensing mechanism comprises a housing positioned in the lower support structure above the feed tray, wherein the housing includes one or more openings for receiving the feed material from the second opening in the feed hopper, and wherein the feed dispensing mechanism includes an auger positioned within the housing that is selectively rotated by a motor operated by the controller to dispense the volume of the feed material.

6. The apparatus of claim 5, wherein the housing includes a tunnel through which the auger extends, wherein the housing includes a discharge opening providing a passageway from the tunnel to the feed tray, and wherein, when the auger is rotated by the motor, the auger drives the feed material into the tunnel.

7. The apparatus of claim 6, wherein the feed dispensing mechanism further comprises a hatch and an actuator actuatable by the controller to move from a first position between the discharge opening and the food tray to a second position away from the discharge opening, whereby the food material in the tunnel when the auger is being rotated is dispensed into the food tray.

8. The apparatus of claim 6, further comprising a second feed tray opposite the food tray in the lower support structure, wherein the feed dispensing mechanism is operable to selectively dispense the feed material from the feed hopper into the second feed tray via the second opening in the body, wherein the sensor assembly senses data for a second animal in the herd accessing the second feed tray, wherein the controller processes the data sensed by the sensor assembly to determine an identity of the second animal and, in response, to first retrieve based on the identity of the second animal a predefined mass of the feed material assigned to the second animal and to second operate the feed dispensing mechanism to dispense into the feed tray a volume of the feed material determined to provide the predefined mass assigned to the second animal, and wherein the feed dispensing mechanism includes a second auger rotated selectively by control signals from the controller to dispense the volume of the feed material via a second discharge opening in the housing.

9. The apparatus of claim 8, wherein the auger and the second auger are arranged to be parallel in the housing and wherein the auger and the second auger are rotated in opposite directions to dispense the feed material from the housing.

10. The apparatus of claim 5, wherein the volume of the feed material is determined by the controller based on a rotation rate of the auger, a predefined volume per unit rotation for the auger, and a rotation time for the auger during the dispensing of the volume of the feed material by the feed dispensing mechanism.

11. The apparatus of claim 10, wherein the volume of the feed material is further determined based on a density of the feed material determined by the controller, prior to operation of the feed dispensing mechanism, based on a weight sensed by the sensor assembly of the feed hopper containing the feed material.

12. The apparatus of claim 1, further comprising auxiliary readers to download onboard or offboard cattle sensor data including data from an activity monitor, a temperature monitor, an activity tag, or a breath sensor, wherein the controller processes the onboard cattle sensor to identify a health problem for an animal accessing the food tray or to modify the mass of the predefined mass dispensed for the animal.

13. An apparatus for dispensing feed material to individual animals of a herd, comprising:
a feed hopper with a first opening for receiving the feed material and with second opening for discharging the feed material;
a lower support structure supporting the feed hopper;
first and second feed trays on opposite sides of the lower support structure;
a feed dispensing mechanism, positioned in the lower support structure, operable to selectively dispense the feed material from the feed hopper into the first and second feed trays via the second opening in the feed hopper;
a sensor assembly sensing data for an animal in the herd accessing one of the first and second feed trays;
a controller processing the data sensed by the sensor assembly to determine an identity of the animal and, in response, to first retrieve based on the identity a predefined mass of the feed material assigned to the animal and to second operate the feed dispensing mechanism to dispense into the one of the first and second feed trays a volume of the feed material to provide the predefined mass, and
wherein the feed dispensing mechanism comprises a housing positioned in the lower support structure above the feed tray, wherein the housing includes one or more openings for receiving the feed material from the feed hopper, wherein the feed dispensing mechanism includes first and second augers positioned to be parallel within the housing, and wherein each of the first and second augers is selectively rotated by a motor operated by the controller to dispense the volume of the feed material.

14. The apparatus of claim 13, wherein the housing includes first and second tunnels through which the first and second augers extend respectively, wherein the housing includes first and second discharge openings providing separate passageways from the first and second tunnels to the first and second feed trays respectively, and wherein, when the first auger is rotated by the motor, the first auger drives the feed material into the first tunnel and when the second auger is rotated by the motor the second auger drives the feed material into the second tunnel.

15. The apparatus of claim 14, wherein the feed dispensing mechanism further comprises first and second hatches positionable over the first and second discharge openings and actuators actuatable by the controller to move the first and second hatches, respectively, to dispense the feed material selectively from one of the first and second tunnels into the first or second food tray.

16. The apparatus of claim 14, wherein the first auger and the second auger are rotated in opposite directions to dispense the feed material from the housing.

17. The apparatus of claim 13, wherein the volume of the feed material is determined by the controller based on a rotation rate of the first and second augers, a predefined volume per unit rotation for each of the first and second augers, and a rotation time for one of the first and second augers during the dispensing of the volume of the feed material by the feed dispensing mechanism.

18. The apparatus of claim 17, wherein the volume of the feed material is further determined based on a density of the feed material determined by the controller, prior to operation of the feed dispensing mechanism, based on a weight sensed by the sensor assembly of the feed hopper containing the feed material.

19. A method of dispensing feed material to individual animals of a herd, comprising:
- at each of a plurality of feed bin assemblies used for feeding the herd, storing a record for each of the animals in the herd including a unique identifier for each of the animals and a predefined mass of feed material for a feeding time period for each of the animals; and
- when one of the animals accesses a food tray on one of the feed bin assemblies and with a control module, first determining the unique identifier for the one of the animals, second retrieving the predefined mass of the feed material associated with the unique identifier, and third operating the one of the feed bin assemblies to dispense a volume of the feed material with a mass less than or equal to the predefined mass,
- further including after the third operating, updating the record associated with the unique identifier to record the mass dispensed from the one of the feed bin assemblies and to generate a remaining mass of the feed material for the feeding time period by subtracting the mass dispensed from the predefined mass of the feed material associated with the unique identifier,
- further including operating the control module of the one of the feed bin assemblies to wirelessly communicate the remaining mass to other ones of the feed bin assemblies for use in updating, at each of the other ones, a local copy of the record associated with the unique identifier.

20. The method of claim 19, wherein the mass of the volume of the feed material dispensed is determined based at least one of a density of the feed material determined by the control module and operations of a feed dispensing mechanism to dispense the volume including rotation rate of an auger and rotation time for the auger.

21. The method of claim 19, wherein the control module determines the volume based on a measure mass of the feed material determined to be present upon a food tray accessed by the animal associated with the unique identifier and on the one of the food bin assemblies.

22. An apparatus for dispensing feed material to individual animals of a herd, comprising:
- a feed hopper with body having a first opening for receiving the feed material into an inner space of the body and having a second opening in a lower portion of the body for discharging the feed material from the inner space of the body;
- a lower support structure supporting the feed hopper;
- a feed tray in the lower support structure;
- a feed dispensing mechanism operable to selectively dispense the feed material from the feed hopper into the feed tray via the second opening in the body;
- a sensor assembly sensing data for an animal in the herd accessing the feed tray; and
- a controller processing the data sensed by the sensor assembly to determine an identity of the animal and, in response, to first retrieve based on the identity a predefined mass of the feed material assigned to the animal and to second operate the feed dispensing mechanism to dispense into the feed tray a volume of the feed material determined to provide the predefined mas,
- wherein the feed dispensing mechanism comprises a housing positioned in the lower support structure above the feed tray, wherein the housing includes one or more openings for receiving the feed material from the second opening in the feed hopper, and wherein the feed dispensing mechanism includes an auger positioned within the housing that is selectively rotated by a motor operated by the controller to dispense the volume of the feed material.

23. The apparatus of claim 22, wherein the sensor assembly includes a weight sensing device for determining a weight of the feed hopper and wherein changes in the weight of the feed hopper are used by the controller to control the feed dispensing mechanism to dispense the volume of the feed material or the weight is communicated to a remote device to facilitate refilling the feed hopper with the feed material.

* * * * *